(12) United States Patent
Srinivasan et al.

(10) Patent No.: US 11,504,009 B2
(45) Date of Patent: Nov. 22, 2022

(54) SYSTEM AND METHOD FOR DOSE CAPTURE WITH FLOW PATCH AND DELIVERY INFOMATICS

(71) Applicant: Embecta Corp., Andover, MA (US)

(72) Inventors: Sudarsan Srinivasan, North Brunswick, NJ (US); Rita Grace Srinivasan, Glen Allen, VA (US)

(73) Assignee: Embecta Corp., Andover, MA (US)

( * ) Notice: Subject to any disclaimer, the term of this patent is extended or adjusted under 35 U.S.C. 154(b) by 393 days.

(21) Appl. No.: 16/095,760

(22) PCT Filed: Apr. 26, 2017

(86) PCT No.: PCT/US2017/029603
§ 371 (c)(1),
(2) Date: Oct. 23, 2018

(87) PCT Pub. No.: WO2017/189707
PCT Pub. Date: Nov. 2, 2017

(65) Prior Publication Data
US 2021/0219845 A1     Jul. 22, 2021

Related U.S. Application Data

(60) Provisional application No. 62/328,702, filed on Apr. 28, 2016.

(51) Int. Cl.
| | |
|---|---|
| *A61B 5/01* | (2006.01) |
| *A61B 5/00* | (2006.01) |
| *A61M 5/142* | (2006.01) |

(52) U.S. Cl.
CPC .............. *A61B 5/01* (2013.01); *A61B 5/0008* (2013.01); *A61B 5/0022* (2013.01);
(Continued)

(58) Field of Classification Search
CPC ....... A61B 5/01; A61B 5/0008; A61B 5/0022; A61B 5/4839; A61B 2562/0271; A61M 5/14248; A61M 5/427
See application file for complete search history.

(56) References Cited

U.S. PATENT DOCUMENTS

| | | |
|---|---|---|
| 6,156,008 A | 12/2000 | Castellano |
| 6,386,050 B1 | 5/2002 | Yin et al. |
| | (Continued) | |

OTHER PUBLICATIONS

European Search Report dated Jul. 18, 2019, which issued in the corresponding European Patent Application No. 17790331.7.
(Continued)

*Primary Examiner* — Patrick Fernandes
*Assistant Examiner* — Liam A Wallace
(74) *Attorney, Agent, or Firm* — Greenberg Traurig, LLP; David J. Dykeman; Roman Fayerberg

(57) ABSTRACT

An injection sensing device (ISD) (e.g., wearable patch) is paired with an external device (e.g., a medication delivery pen and/or smart phone, iPad, computer) via wireless link or wireline connection. The ISD senses fluctuations in local skin temperature during an injection and provides to the external device captured data from the sensor relating to medicine delivery to a patient to ensure complete delivery and minimize MDD misuse or malfunction or inaccuracies in dosing. The ISD or external device can use captured data and corresponding time stamps to determine flow informatics such as flow rate, total dose delivered, and dose completion status. An LED on the ISD indicates delivery in progress and/or delivery completion.

16 Claims, 10 Drawing Sheets

(52) U.S. Cl.
CPC .... *A61B 5/4839* (2013.01); *A61B 2562/0271* (2013.01); *A61M 5/14248* (2013.01)

(56) References Cited

U.S. PATENT DOCUMENTS

| | | |
|---|---|---|
| 2004/0153031 A1* | 8/2004 | Van Kaauwen ...... A61M 5/427 604/116 |
| 2008/0269570 A1 | 10/2008 | Leung et al. |
| 2010/0049126 A1 | 2/2010 | Bronfeld et al. |
| 2010/0060464 A1 | 3/2010 | Larsen |
| 2011/0184342 A1 | 7/2011 | Pesach et al. |
| 2011/0288527 A1 | 11/2011 | Pesach et al. |
| 2011/0313351 A1 | 12/2011 | Kamen et al. |
| 2013/0085357 A1* | 4/2013 | Huber ................ A61B 5/14542 600/364 |
| 2013/0237955 A1* | 9/2013 | Neta ................ A61M 5/16831 604/500 |
| 2014/0207099 A1 | 7/2014 | Nagar et al. |
| 2015/0246179 A1 | 9/2015 | Zur |

OTHER PUBLICATIONS

International Search Report dated Jul. 26, 2017, which issued in corresponding PCT Patent Application PCT/US217/029603.

* cited by examiner

SYSTEM AND METHOD FOR DOSE CAPTURE WITH FLOW PATCH AND DELIVERY INFOMATICS

FIELD OF THE INVENTION

Embodiments of the invention relate to a smart delivery device (e.g., wearable patch) for use with a syringe or medication pen that senses and provides medication delivery infomatics (e.g., medication delivery flow, delivery completion status, time of delivery, and so on) to a user.

BACKGROUND OF THE INVENTION

Medication pens and syringes are typically used to inject medication such as insulin into a patient or user. Inefficiencies and inconveniences can arise during self-injection, as well as inaccuracies in dosing such as from misuse or malfunctioning of the medication pen or syringe. For example, sometimes an insulin user prematurely removes the insulin injection device from the injection site before the complete prescribed medication dosage is delivered. This can result in the user or patient not taking a full dose of medication and ultimately impacting his or her glucose control. A key unmet need in diabetes management is to track how much medication was taken by a user and know when all the medication is delivered to the user's body. A need exists for a device and method to monitor the flow of a delivered drug from the medication delivery device to the patient's body and to provide delivery infomatics to the patient and/or a healthcare provider or caregiver.

SUMMARY OF THE INVENTION

It is an aspect of illustrative embodiments of the present invention to provide an injection sensing device (ISD) for use with a medication delivery device, wherein the injection sensing device comprises a thermal sensor configured to be applied to the skin of a patient and proximal to an injection site and to sense a change in temperature of the patient at the injection site and output corresponding sensor data; and a processing device configured to receive the sensor data from the sensor and perform a designated operation when the sensor data indicates that the patient's temperature sensed at the injection site has changed by a For example, in accordance with an aspect of the present invention, the processing device is configured to operate an indicator to indicate to the patient that medication delivery via the administration of the injection is complete in response to the sensor data indicating that the patient's temperature sensed at the injection site began decreasing upon initiation of the injection and thereafter increasing to at least a designated amount in relation to the administration of the injection.

In accordance with another aspect of the present invention, the ISD further comprises a wireless communication circuit configured to transmit the sensor data from the ISD to an external device on a wireless link. For example, the processing device can be configured, when the external device is paired with the ISD, to transmit the sensor data to the external device via the wireless link during delivery of the medication to the patient.

In accordance with an aspect of the present invention, an ISD software application (e.g., an ISD app for downloading to a mobile phone, iPad or other computing device) is provided to the external device to configure the external device to analyze the sensor data comprising sensed temperatures at the injection site and corresponding time stamps to determine flow rate of the medication from the medication delivery device to the patient. In addition, the ISD software application can configure the external device to determine delivery infomatics using the sensor data comprising at least one of completion of medication delivery, completion of prescribed dosage, total amount of medication delivered, and time of medication delivery.

In accordance with another aspect of the present invention, the processing device is configured to associate time stamps with respective sensor data and to analyze the sensor data comprising sensed temperatures at the injection site and corresponding time stamps to determine flow rate of the medication from the medication delivery device to the patient. In addition, the processing device can be configured to determine delivery infomatics using the sensor data comprising at least one of completion of medication delivery, completion of prescribed dosage, total amount of medication delivered, and time of medication delivery.

Additional and/or other aspects and advantages of the present invention will be set forth in the description that follows, or will be apparent from the description, or may be learned by practice of the invention. The present invention may comprise injection sensing devices or ISDs (e.g., a wearable patch) and/or connected smart devices (e.g., mobile phone or computer with ISD app) and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above aspects and features of the present invention will be more apparent from the description for the illustrative embodiments of the present invention taken with reference to the accompanying drawings, in which.

Throughout the drawing figures, like reference numbers will be understood to refer to like elements, features and structures.

DETAILED DESCRIPTION OF ILLUSTRATIVE EMBODIMENTS

Figure 1:
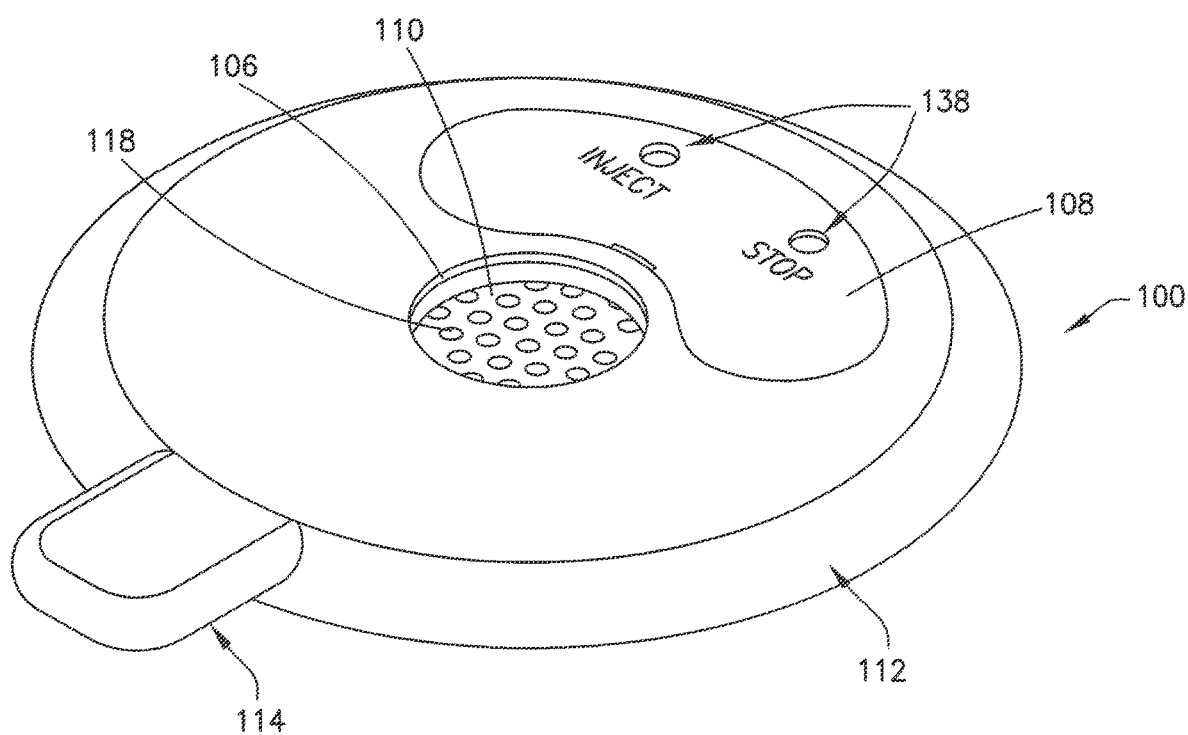
FIG. 1 is a perspective view of an injection sensing device in accordance with an illustrative embodiment of the present invention.
Figure 2A:
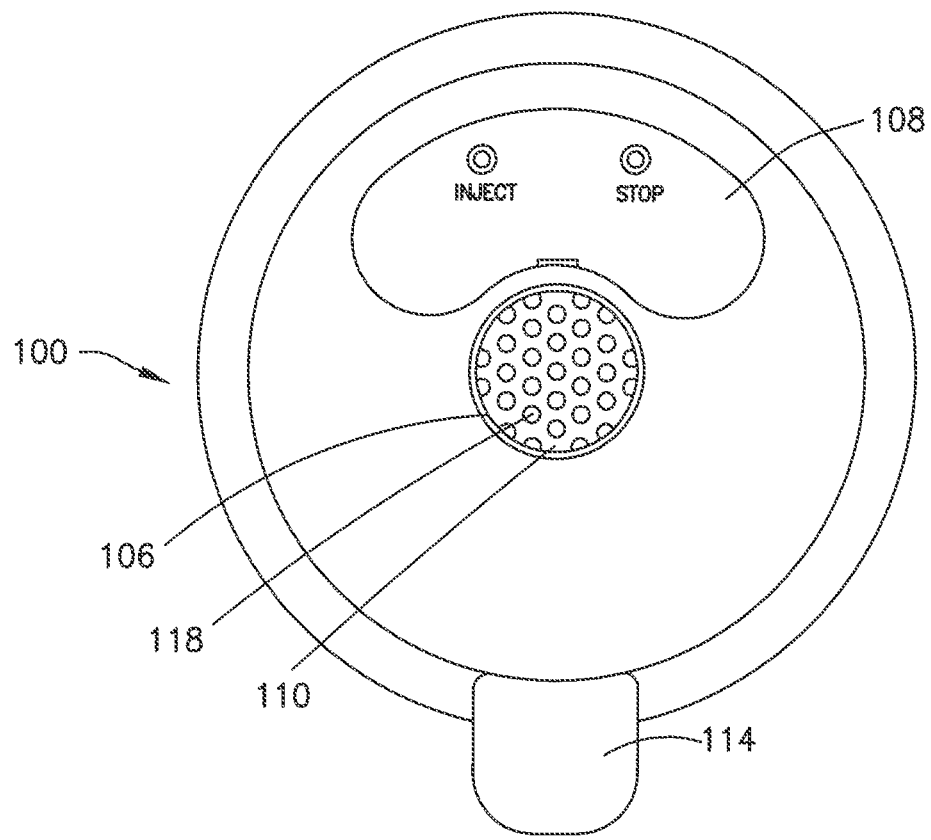
FIGS. 2A and 2B are, respectively a top view and a side elevational view of the injection sensing device in FIG. 1.
Figure 2B:
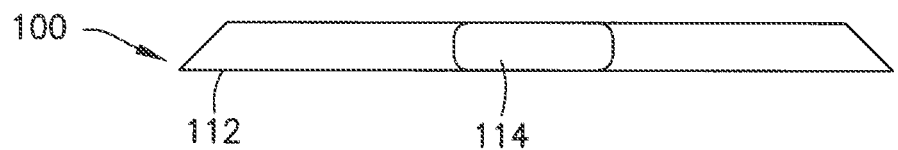
Figure 3:
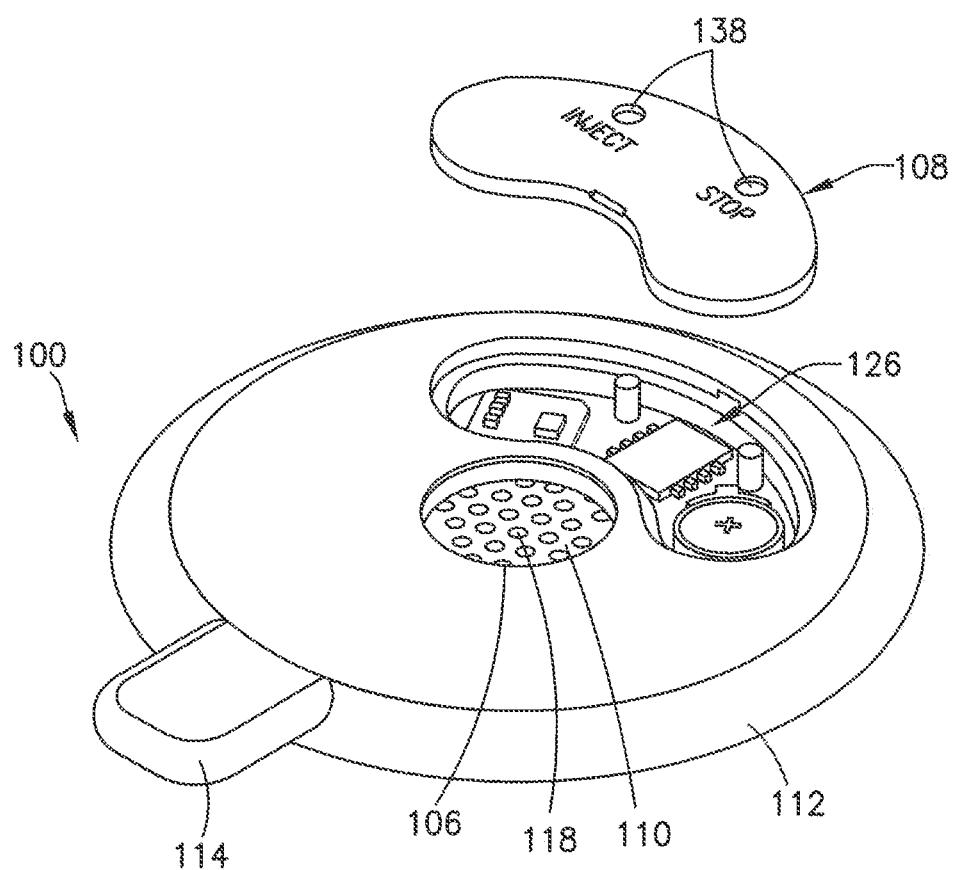
FIG. 3 is a perspective view of the injection sensing device in FIG. 1 with a cover removed to expose embedded electronics in accordance with an illustrative embodiment of the present invention.
Figure 4:
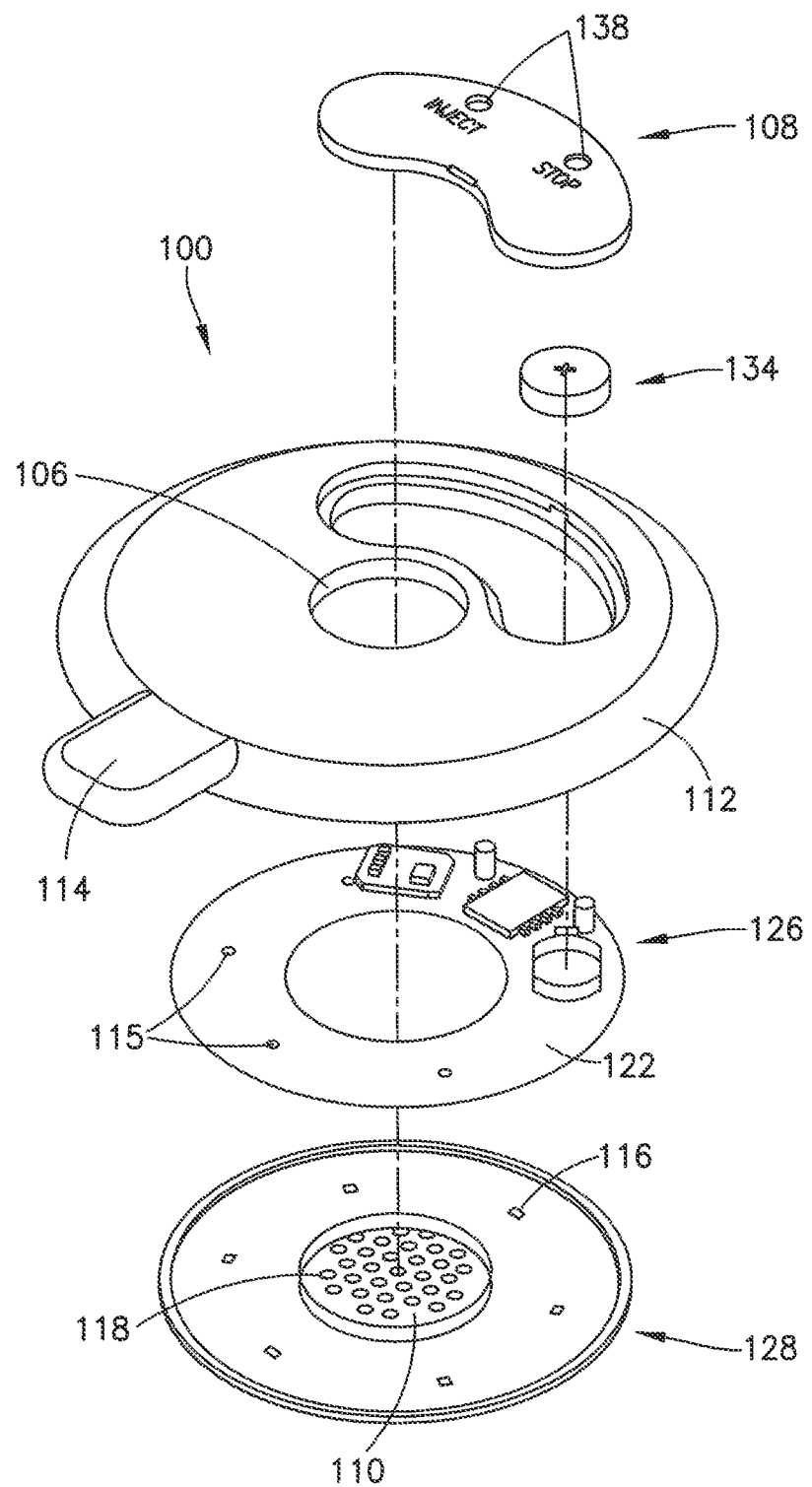
FIG. 4 is an exploded view of the injection sensing device in FIG. 1.

Reference will now be made in detail to embodiments of the present invention, which are depicted in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 6:
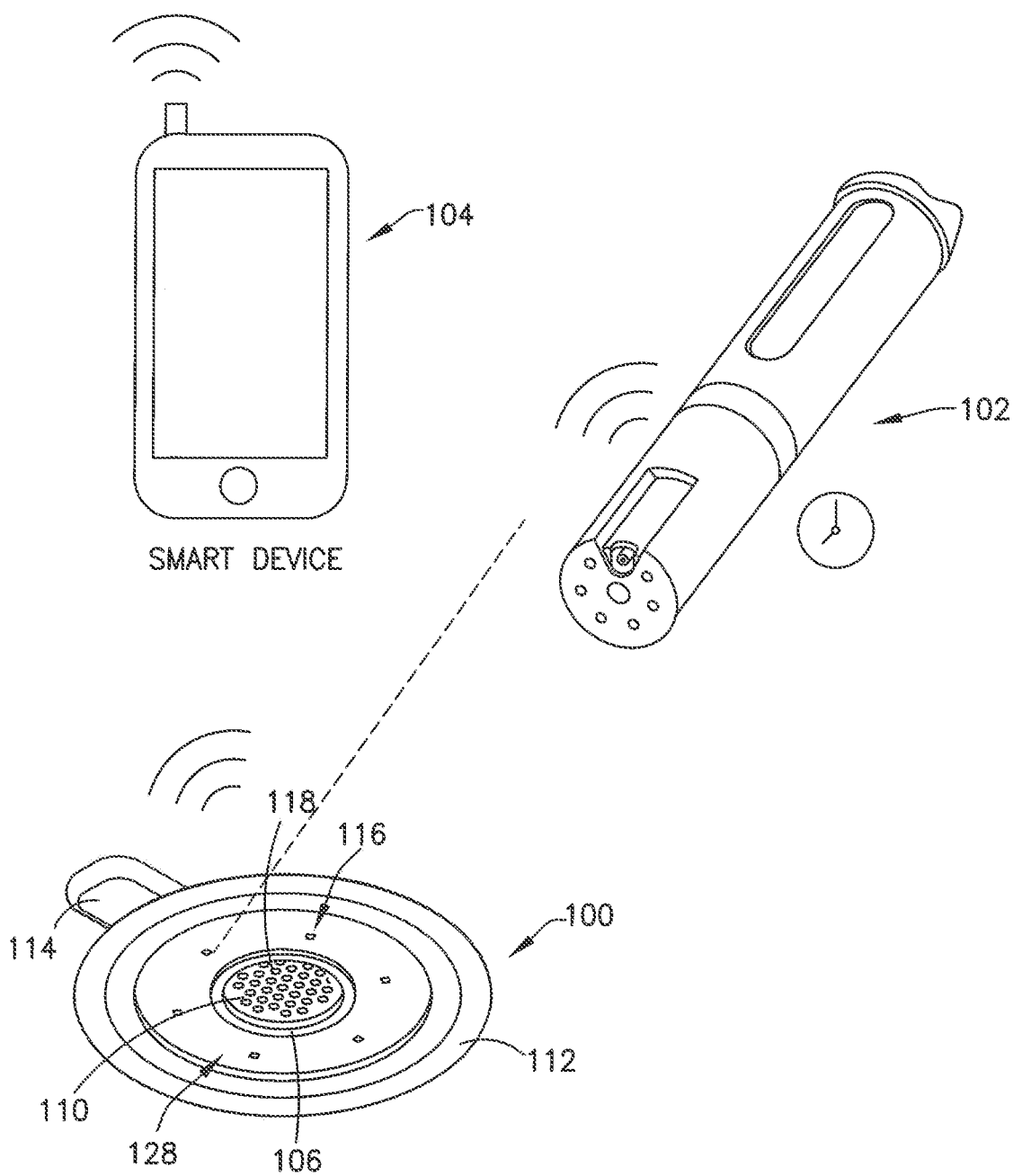
FIG. 6 is a perspective view of the injection sensing device in FIG. 1 operating in conjunction with a medicine delivery device, which can have a needle extend through one of several injection ports accessible from an injection port cutout, and in conjunction with a smart device in accordance with an illustrative embodiment of the present invention.
Figure 7:
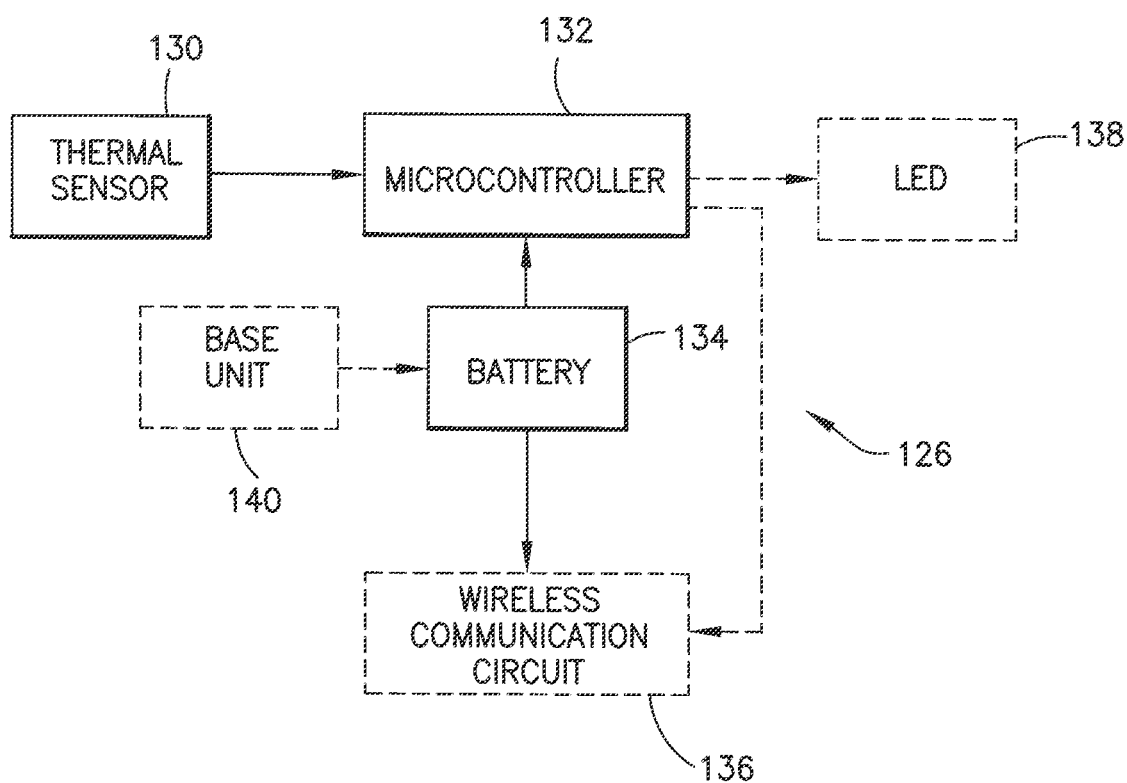
FIG. 7 is a block diagram of electronic components in an injection sensing device in accordance with an illustrative embodiment of the present invention.

In accordance with illustrative embodiments of the present invention, an injection sensing device ISD 100 is configured to sense data related to medication delivery and indicate sensed delivery data or dose capture data (e.g., via an LED or other on-board user interface), and/or communicate sensed delivery data or dose capture data to an external device (e.g., a medication delivery pen 102 and/or a connected device 104 such as mobile phone per FIG. 6) for output to a user (e.g., to confirm progress and/or completion of delivery of medicine by a medicine delivery device). Dose capture at the time of delivery represents advantages over existing delivery systems that do not capture dose information at all, or do so in a limited manner and not immediately/concurrently with dose delivery. For example, a conventional medication delivery pen employs a dial by which a user enters a prescribed amount of medication to be delivered. The pen is configured to deliver an amount of medication that corresponds to the dialed input; however, the pen has no means by which to confirm that the prescribed amount of medication was actually delivered. For example, if the medication delivery pen is malfunctioning or misused, a user may not realize that he or she is not receiving the prescribed amount. For example, a user may not hold the pen needle long enough to complete the prescribed delivery, or may misuse device and cause a leak, thereby preventing administration of full dose as prescribed.

With reference to FIGS. 1, 2A, 2B 3, 4, 5A, 5B, 5C, 6 and 7, an injection sensing device (ISD) 100 is provided and is described further below for use with a medicine delivery device (MDD) 102 that delivers fluid such as a medicine (e.g., insulin) to a user, and optionally for use with a connected device 104. The medicine delivery device 102 can be, for example, a medicine pen or a syringe. The connected device 104 can be, for example, a mobile phone, laptop, iPad or other processing device that can, for example, communicate (e.g., wirelessly) with the ISD 100 and/or the MDD 102.

In the illustrative embodiments of FIGS. 1, 2A, 2B 3, 4, 5A, 5B, 5C, 6 and 7, the ISD 100 is a wearable patch applied to a patient's skin over an area of skin on the patient's body that comprises one or more medication injection sites. For example, the ISD 100 is implemented as a reusable patch wherein the bottom of the patch per FIG. 3 has a portion thereof that is an adhesive layer 112 (e.g., a medical adhesive tape material) that adheres to the patient's skin, and another portion (e.g., a thermal conductive layer 128) that carries part of a temperature sensor described below and does not necessarily adhere to the patient's skin. The adhesive layer 112 and the thermal conductive layer 128 can be comprised of flexible material that can contour a patient when applied to the skin over a particular body area (e.g., abdomen, thigh). In the illustrated embodiment, the ISD 100 employs the adhesive layer 112 around its entire perimeter. The adhesive layer 112, however, can be employed in sections along the perimeter that are not necessarily continuous, and in sections within the thermal conductive layer 128 for affixing to the patient's skin in a manner that is conveniently removable yet secure when the patient desires to wear the ISD 100. The ISD 100 can be provided with a peel flap 114 extending from the perimeter of the adhesive patch to provide the patient with a conveniently means to lift the ISD 100 from the patient's skin.

With reference to FIGS. 4, 5A, 5B, 5C, 6 and 7, the ISD 100 employs electronics 126 comprising a thermal sensor 130. In accordance with an illustrative embodiment of the present invention, the thermal sensor 130 can sense temperatures at least from 0° C. to 50° C., or some other greater range including 0° C. to 50° C. or a smaller range therebetween, and particularly including typical body temperatures of patient's employing the IDS 100 and insulin delivery conditions (e.g., at least 20° C. to 28° C.). The thermal sensor 130 can be implemented, for example, using a thermistor-based approach or a temperature sensing integrated circuit or IC-based approach as exemplified in connection with FIGS. 8 and 9.

The thermal sensor 130 can be implemented, for example, as thermistors 116 disposed on the bottom of the thermal conductive layer 128 of the ISD 100. The thermistors 116 are coupled to electronics 126 provided in the ISD 100 (e.g., by conductive nodes or traces indicated generally at 115 or other coupling means in the printed circuit board 122). The electronics 126 comprise, for example, a processing device 132 such as a microprocessor, microcontroller, a programmable gate array (e.g., FPGA) or application specific integrated circuit (ASIC). The electronics also comprise one or more light emitting diode (LED) indicators 138 and/or a wireless communication circuit 136, and a battery 134 for providing power to the other electronics devices. Different wireless communication methods can be used such as Bluetooth™ or near field communication (NFC) technology. The ISD 100 may need to be within 10 meters of the other device 102 and/or 104 if paired via Bluetooth™ whereas the communicating devices 100 and 102 and/or 104 may need to be more proximal to each other (e.g., on the order of 10 centimeters apart or less) for NFC pairing.

With reference to FIGS. 1, 2A, 2B, 3 and 4, the top of the ISD 100 can be provided with a cover 108 except for an injection port cutout 106 that exposes a section of the patient's skin. A portion of the cover 108 is removed in FIG. 3 for illustrative purposes to show electronics 126 such as the microcontroller 132, battery 134 and optional wireless communication integrated circuit 136. One or more LEDs 138 can also be provided on the top of the ISD 100 so as to be visible to a user when the ISD 100 is adhered to the patient's skin. The cover can be a clear or transparent material, or be a nontransparent material that allows an LED output to be visible. A single LED 138 can be operated to show, for example, when dosing is complete (e.g., illuminated when dosing is initiated and turned off after dosing is complete). In accordance with another example, a green LED can be operated by the microcontroller 132 to turn on when the ISD 100 is ready for use (e.g., the electronics 126 are powered by the battery 134), and to flash during an injection. This way, a user knows when the ISD is charged and operational. A red LED can be illuminated or flashed when an injection is completed for example.

The cutout section 106 of the ISD 100 can be provided with a perforated film 110 and one or more through-holes 118. The perforated film facilitates allowing air to the patient's skin, and the holes 118 can serve as guidance for needle placement for medication delivery. Film 110 can also facilitate retaining more consistent temperature of the patient's skin in the cutout section 106 relative to the skin covered by layers or portions 128 and 112. Although the holes 118 can be optional (e.g., a user can pierce the film 110 with the needle of a MDD 102 anywhere within cutout section 106), the holes 118 provide a visual guide to assist user in spacing injections far enough apart from one another, and optionally arranged with the respect to each other in a pattern, to minimize the occurrence of lipodystrophy such as "lipos," which is a term corresponding to thickening of tissue (e.g., lumps, dents, or red or swollen subcutaneous tissue that can occur at an injection site). In other words, the film 110 with pattern of holes 118 allows the user to rotate the injection site within a body area, which is important in delivery of insulin to ensure the patient does not inject using the same injection site repeatedly within a short period of time and risk development of lipos.

Figures 5A, 5B:
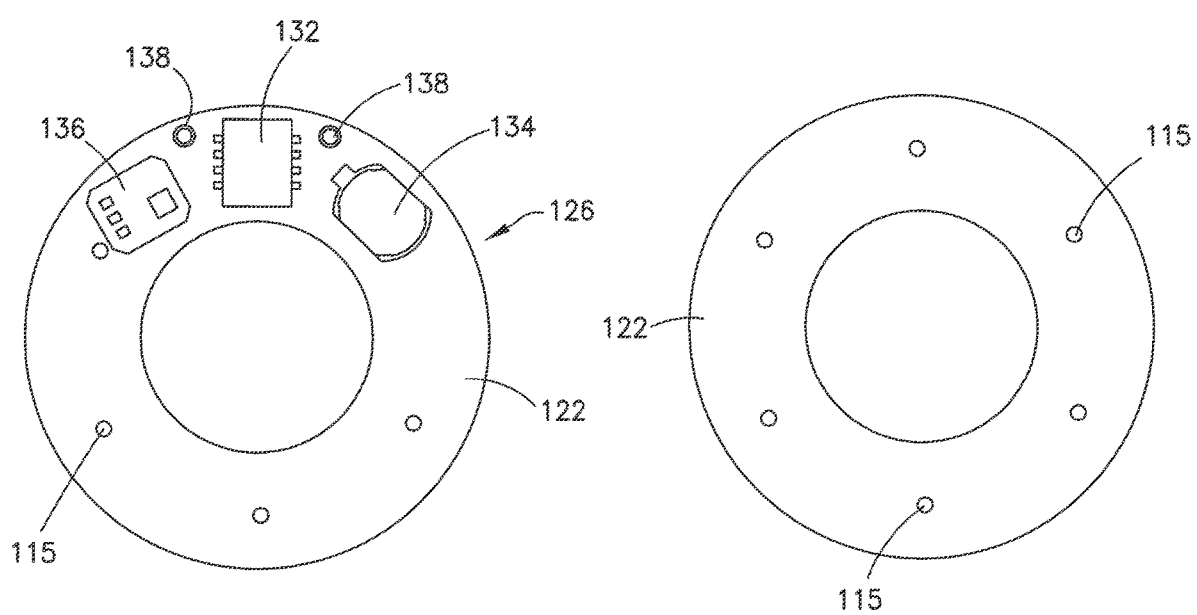
FIGS. 5A, 5B and 5C are, respectively, top, bottom and exploded views of the embedded electronics of the injection sensing device in FIG. 1.
Figure 5C:
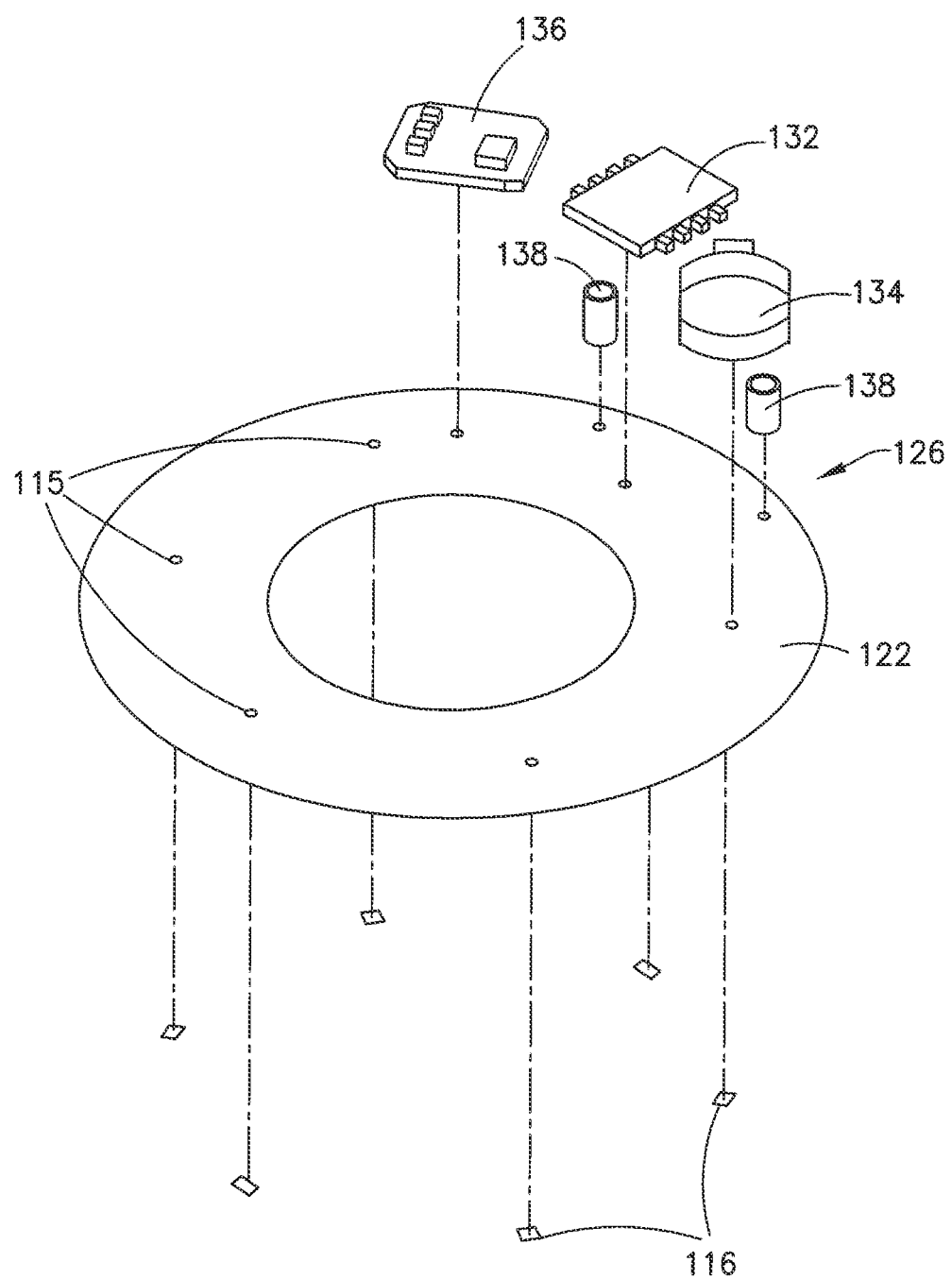

In the illustrative embodiment, the ISD 100 is round and comprises a ring of thermistors 116 in a radial arrangement to sense temperature of the patient's skin around an injection site in the area defined by the cutout 106 in a substantially evenly distributed manner to ensure that any temperature changes around the injection site can be detected. Other shapes besides a ring for a thermal conductive layer 128 can be used, however, and the cutout 106 need not be centered relative to the ISD 100. As stated above with respect to the adhesive layer 112, the sensing materials can be distributed within the footprint or perimeter of the ISD in various sections and in accordance with various patterns for sensing locations. In the illustrative embodiment, the ISD 100 is round and about 2 inches in diameter. The ISD 100 itself need not be round in shape but can also be rectangular, square or even an irregular shape that anatomically contours an area of the body commonly used for injections such as the thighs, buttocks, backs of the arms and so on. With reference to FIGS. 5A, 5B and 5C, the electronics 126 can be mounted on a flexible printed circuit board (PCB) 122 that flexes to fit on the skin of a patient's body and at any orientation. Regardless of ISD 100 shape, the thermal conductive layer 128 and its corresponding thermal sensing materials or devices (e.g., thermistors 116 or temperature sensing integrated circuits) can be advantageously distributed within the profile of the ISD 100 for optimal thermal sensing of the body area upon an injection.

Operation of the ISD 100 will now be described. Generally, during use, local temperature of a patient's skin near an injection site is changing (e.g., decreasing) when the patient is injecting. For example, as a drug that is at room temperature (20° C.) enters the skin, which is typically at 38° C., the local skin temperature changes rapidly and lowers. This change in temperature indicates the flow of that drug from the MDD 102 into the patient's skin. When the flow of the drug stops, the local temperature begins equilibrating by starting to rise. This rise in temperature indicates the flow has ended, and the electronics of the ISD 100 can then inform the user with an audible sound and/or a visual indication that the flow has stopped and the injection is complete.

For example, the output of the thermal sensor 130 is used to detect fluctuations of the detected local skin temperature, and the processing circuit 132 analyzes these fluctuations relative to an injection (e.g., using time stamps for changes in detected temperature). The processing circuit 132 can be configured to drive the LED 138 to indicate when an injection is complete, such as when the detected skin temperature drops from approximately 38° C. to a selected threshold temperature and then rises above the selected threshold temperature by a designated amount within a designated amount of time. An audible indicator can also be driven. The LED and/or the audible indicator can be provided on the ISD 100 itself or, in the interest of minimizing the profile, complexity and cost of the ISD 100, can be provided in the MDD 102 or a connected device 104 that is wirelessly connected to the ISD 100. The patient can then remove the MDD 102 from the skin.

The temperature sensing, processing and output generating aspects of the ISD 100 are advantageous in that the ISD 100 ensures the full dose delivery of the drug into the body and the MDD 102 is not being misused (e.g., removed from the skin too early during an injection). Also, the time that the dose was delivered can also be recorded, and this information can be transmitted to a user via the wireless communications circuit 136 to a smart phone 104 or other similar connected device 104. This allows a user (e.g., the patient or a caregiver) to track the number and times of the doses administered to the patient. For example, a software application or "app" for Android and/or iOS devices 104 can be provided to manage such delivery infomatics as when a dose is taken or administered and can include the time a dose was initiated (e.g., when the detected local skin temperature drops a designated amount), and a time associated with the end of the dose (e.g., when the detected local skin temperature rises a designated amount after dose initiation). The time stamps can be provided by a real-time clock in the electronics 126 of the ISD 100 or, if the ISD 100 and MDD 102 are paired in real-time relative to an injection event, the ISD 100 can communicate sensor data from the thermal sensor 130 wirelessly to the MDD 102 and/or a smart phone 104 and in real-time, and the MDD 102 and/or a smart phone 104 or other connected device can associate time stamps with the received sensor data. Further, the MDD 102 and/or the smart phone 104 can be programmed (e.g., via an injection sensing app) to analyze the sensor data and provide delivery informatics such as medicine delivery progress and/or completion status.

The ISD 100 can also be configured to determine the amount of a dose that is delivered to the patient (e.g., to confirm that the prescribed dosage was actually delivered to the patient for prescription compliance monitoring and to ensure the MDD 102 is not malfunctioning). In other words, the rate at which the flow of medication is going through the patient's skin can be measured by the rate at which the local skin temperature is changing, which provides the means to calculate the total volume delivered. For example, the processing device 132 can be configured to analyze and relate fluctuations of the detected local skin temperature (e.g., detected local skin temperature changes and corresponding time stamps) to a flow rate. For example, as the change in temperature is sensed, the area under a curve representing sensed temperature over time can be calculated, which can be considered proportional to the volume of the drug delivered or the dose delivered. For example, the calculated area being proportional to delivered volume is generally true when the user applies an essentially constant thumb force on the medication delivery device and when the time of dispense is essentially constant for a given dose. In this case, the drug is flowing at an essentially constant flow rate and the change in temperature over the time can be plotted and the area under the curve (AUC) can be calculated to predict or estimate the dose delivered.

As stated above, the flow rate data determined by the processing device 132, or a processing device on the MDD 102 or connected device 104, can be used for volume sensing to determine total delivered amount. To minimize complexity and cost of the ISD 100, the ISD 100 can wirelessly transmit temperature output data to the MDD 102 and/or the connected device 104 (e.g., a smart phone) in essentially real-time. The ISD 100, MDD 102 and/or the connected device 104 (e.g., a smart phone) can be configured to provide time stamps. If the ISD 100 has a clock, it can transmit the temperature output data and corresponding time stamps to the MDD 102 and/or the connected device 104. The MDD 102 and/or the connected device 104, in turn, can be programmed to determine the flow rate and perform total volume delivered analysis.

The ISD 100 can be a disposable patch that is removed and discarded when the battery 134's power is drained. Alternatively, the ISD 100 can be a reusable patch that can be worn multiple times. The reusable patch is recharged after use with a base unit 140 (FIG. 7) that provides the power to recharge to the battery 134. Alternatively, the PCB 122 associated battery contacts and the battery 134 under the cover 108 can be configured to allow the battery 134 to be replaceable.

Figure 8:
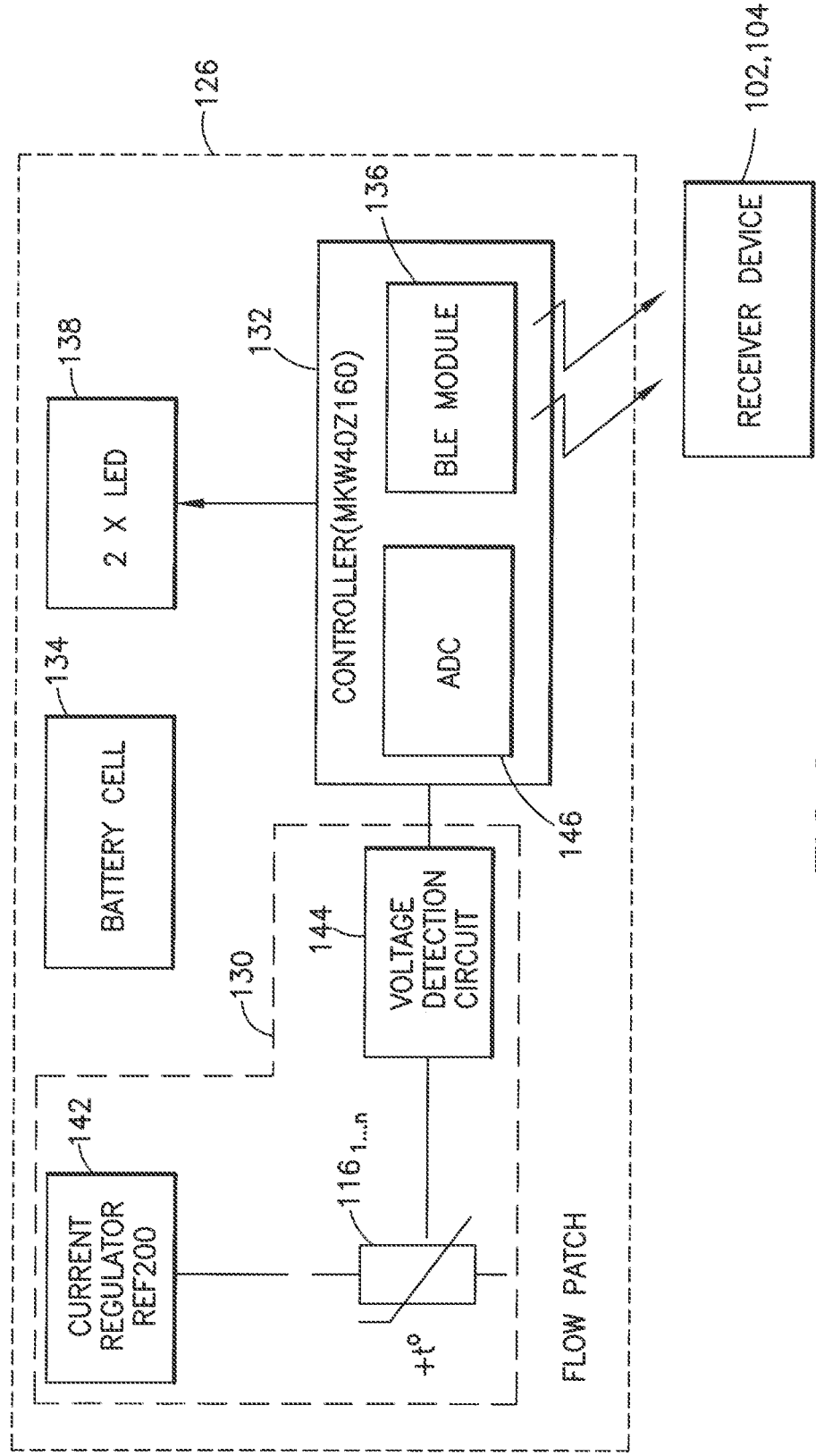
FIG. 8 is a block diagram of electronic components in an injection sensing device using one type of thermal sensor in accordance with an illustrative embodiment of the present invention.

FIG. 8 illustrates electronics 126 of an ISD 100 that employs a thermistor-based approach to the thermal sensor 130 in accordance with an illustrative embodiment of the present invention. A current regulator 142 is used for producing 100 uA current to protect the thermistors $116_1 \ldots 116_n$ from self-heating error. A voltage detection circuit 144 converts the temperature at each thermistor to analog voltage level. The microcontroller 132 processes the temperature signal corresponding to the sensor data (e.g., to determine delivery completion). The microcontroller 132 can have, for example, an inbuilt analog-to-digital converter (ADC) 146 and the wireless communication circuit 136 (e.g., low energy Bluetooth® or BLE®) such as the MKW40Z160 from Freescale or CC2640 from Texas Instruments, or have separate ADC and wireless communication components. Data can be transferred from the microcontroller 132 to a receiver (e.g., in the MDD 102 and/or a smart device 104) for drug flow notification and other delivery infomatics (e.g., delivery rate and/or total volume delivered). As stated above, one or two LEDs 138 can be driven for indication of drug delivery or other conditions such as operational and charged state of the ISD 100.

Figure 9:
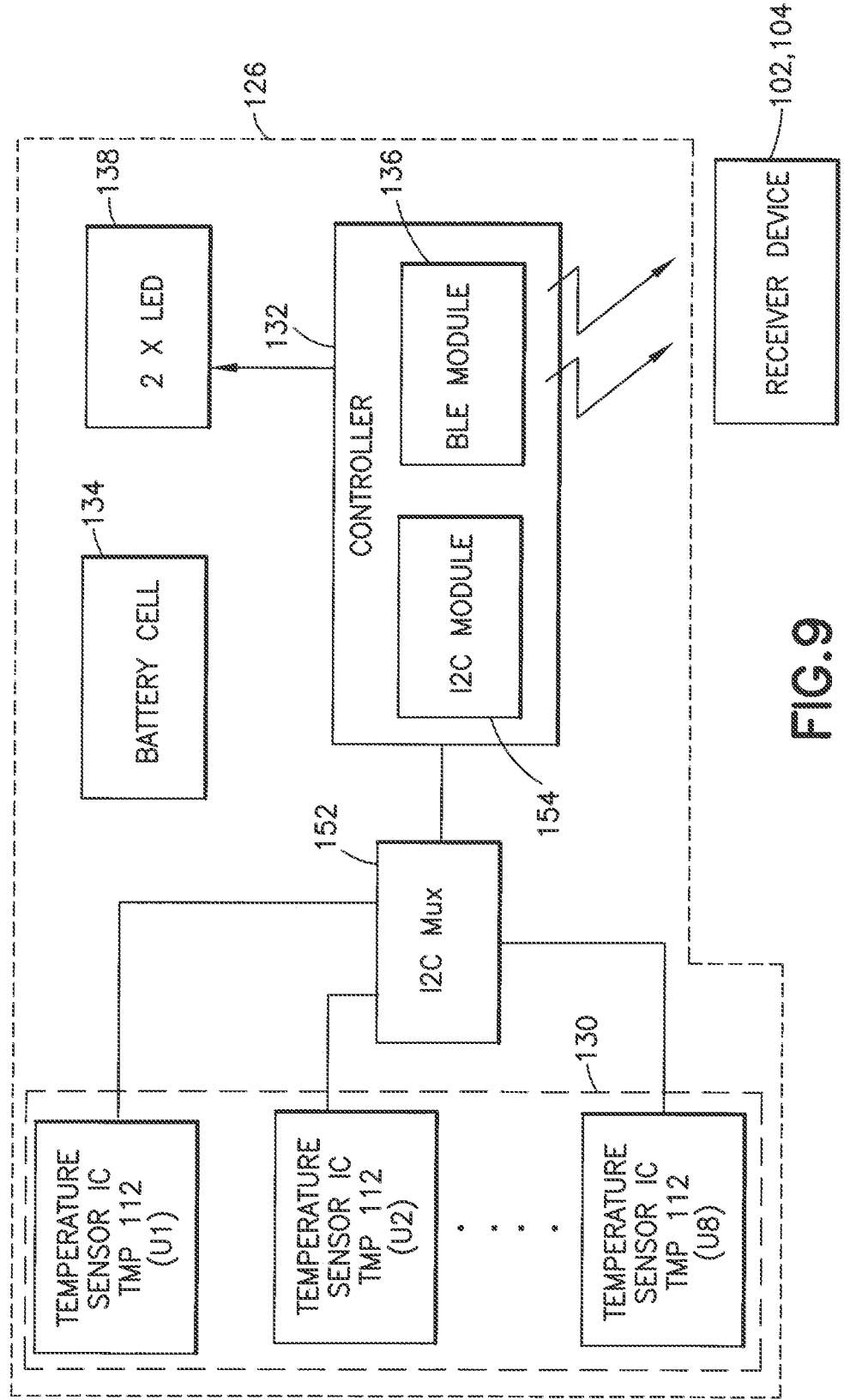
FIG. 9 is a block diagram of electronic components in an injection sensing device using another type of thermal sensor in accordance with another illustrative embodiment of the present invention.

FIG. 9 illustrates electronics 126 of an ISD 100 that employs a temperature sensor IC-based approach to the thermal sensor 130 in accordance with another illustrative embodiment of the present invention. An I2C multiplexor (mux) 152 and corresponding I2C module 154 are provided to interface multiple sensors (e.g., TMP112s U1 through U8) to the microcontroller 132. Temperature is converted to binary through the TMP112. The microcontroller 132 processes the sensor data (e.g., to determine delivery progress and/or completion). The microcontroller 132 can have, for example, an inbuilt wireless communication circuit 136 (e.g., low energy Bluetooth® or BLE®), or have separate wireless communication components. Data can be transferred from the microcontroller 132 to a receiver (e.g., in the MDD 102 and/or a smart device 104) for drug flow notification and other delivery infomatics (e.g., delivery rate and/or total volume delivered). As stated above, one or two LEDs 138 can be driven for indication of drug delivery or other conditions such as operational and charged state of the ISD 100. The temperature sensor IC-based approach to the thermal sensor 130 is advantageous because the thermal sensor 130 can operate more accurately with 0.5 C tolerance than other thermal sensing approaches, and the placement of the sensors (e.g., U1 through U8) in an ISD 100 is relatively easy.

Illustrative embodiments of the present invention provide an advantageous means to monitor the flow of a drug from a medication delivery device (MDD) 102 to the body by measuring the change in local body temperature at or near the injection site as the drug is dispensed from the MDD through the patient's skin. Relatively simple visual indicators can be used to indicate to a user when the flow from the MDD 102 is occurring and when the flow of the drug from the MDD to the patient stops. Relatively simple informatics can be collected and stored (e.g., when the dose is taken, the time of dose, end of dose, and the like). In addition, the rate at which the skin temperature changes can also be measured to correlate the flow rate from the device into the skin. The total amount of dose or volume delivered can be calculated, for example, by relating fluctuations of the detected local skin temperature to a flow rate as described above, and using the area under a curve representing sensed temperature over time as being proportional to the volume of the drug delivered or the dose delivered. These features help the patient to monitor and control his or her glucose level better, and allows the patient to take the full dose by not prematurely removing the device before the full dose is delivered. For example, the ISD 100 and/or the MDD 102 or connected device 104 can measure the total flow through the skin and record the amount of dose taken by the patient. The flow information and total flow information can be used track and monitor compliance of the patient with the prescribed doses and/or injection regimen.

For example, in accordance with an embodiment of the present invention, the connected device 104 can be provided with an app or otherwise programmed or configured to receive dose capture data from a connected or paired ISD 100 or delivery device 102 and, for example, to confirm a designated dose was effectively delivered based on detected flow data received from the delivery device. For example, a prescribed diabetes management regimen of 20 units of insulin 3 times per day can be programmed into the app of a smart device. If the user dials the dose incorrectly into a connected or paired medication pen 102 relative to prescribed regimen (e.g., 10 units instead of 20 units), the app on phone 104 can generate an alarm to alert user when the capture dose data indicates that the detected actual delivered amount is different from the prescribed amount. This significantly reduces user mishandling of a delivery device 102 and provides timely detection of a malfunctioning delivery device 102. This represents a significant advantage over conventional delivery devices, where a user does not hold the pen needle long enough to complete delivery, or misuses the device and causes it to leak, for example. Further, if a dose is skipped altogether, the app can alarm the user or caregiver (e.g., parent) by having the smart device send a text to the caregiver's mobile phone. In addition, the smart phone 104 delivery data app aggregates important delivery data and can share it with healthcare providers, insurance providers, and so on.

The ISD 100 and MDD 102 and/or connected device 104 can have different combinations of hardware and software capabilities or features that impact the delivery infomatics. The data transfer can differ depending on when and how data transfer occurs between the ISD 100 and its associated other connected device 102 and/or 104. For example, the ISD 100 can transfer data regarding drug delivery status (e.g., complete or incomplete) or other delivery infomatics (e.g., rate, timing) in real-time (e.g., during injection) or at any time such as after injection when disconnected devices are eventually paired or otherwise connected or scanned. The communication connectivity can be wireless or wired. Different wireless connectivity methods can be used (e.g., Bluetooth™ or WiFi or near field communication (NFC) technology) which can, in turn, impact device pairing if needed and need for proximity of the ISD 100 to the other connected device 102 and/or 104. The timing of data transfer can be impacted depending on whether or not the ISD 100 and the devices 102 and/or 104 has a time recording capability or not.

As stated above, an ISD software application (e.g., an ISD app for downloading to a mobile phone, iPad or other computing device) is provided to the external device 104 to configure the external device 104 to analyze the sensor data, and determine and output delivery infomatics comprising at least one of completion of medication delivery, completion of prescribed dosage, total amount of medication delivered, and time of medication delivery based on the sensor data. The ISD app can be provided with other operations such as generating reminders for the patient to dose based on stored information comprising a prescribed medication delivery regimen for that patient, as well as reminders when the patient has missed a prescribed dose. The ISD app can also configure the external device 104 to share delivery informatics (e.g., detected doses and optionally delivered amounts, and time stamps) to the connected devices of other members of the patient's healthcare team (e.g., healthcare providers, caregivers, and so on) via WiFi or through a cloud, for example.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed. Accordingly, additional embodiments are possible and are intended to be encompassed within this specification and the scope of the invention. The specification describes specific examples to accomplish a more general goal that may be accomplished in another way.

The invention claimed is:

1. An injection sensing device (ISD) for use with a medication delivery device, comprising:
   a thermal sensor configured to be applied to the skin of a patient and proximal to an injection site and to sense a change in temperature of the patient at the injection site and output corresponding sensor data;
   a processing device configured to receive the sensor data from the thermal sensor and perform a designated operation when the processing device determines from the sensor data that the patient's temperature sensed at the injection site has changed by a designated amount relative to administration of an injection; and
   an indicator, wherein the processing device is configured to perform the designated operation by operating the indicator to indicate to the patient that medication delivery via the administration of the injection is complete in response to the processing device determining that the sensor data indicates that the patient's temperature sensed at the injection site began decreasing upon initiation of the injection and thereafter increasing to at least a designated amount in relation to the administration of the injection.

2. The injection sensing device of claim 1, further comprising a wireless communication circuit connected to the processing device and configured to transmit the sensor data from at least one of the thermal sensor and the processing device to an external device on a wireless link.

3. The injection sensing device of claim 2, wherein the wireless communication circuit is configured to pair with the external device, and to transmit the sensor data to the external device via the wireless link during delivery of medication to the patient.

4. The injection sensing device of claim 2, further comprising an ISD software application provided to the external device to configure the external device to analyze the sensor data from the ISD comprising sensed temperatures at the injection site and corresponding time stamps to determine flow rate of medication from the medication delivery device to the patient.

5. The injection sensing device of claim 4, wherein the ISD software application configures the external device to generate a curve representing determined changes in sensed temperatures at the injection site over time and calculate area under the curve to estimate a delivered dose from the medication delivery device.

6. The injection sensing device of claim 2, further comprising an ISD software application provided to the external device that configures the external device to determine delivery infomatics using the sensor data comprising at least one of completion of medication delivery, completion of prescribed dosage, total amount of medication delivered, and time of medication delivery.

7. The injection sensing device of claim 2, further comprising an ISD software application provided to the external device that configures the external device to perform at least one of a plurality of operations comprising (a) determine from a stored prescribed medication delivery regimen when a dose is needed and generate a corresponding reminder to the patient, (b) determine from a stored prescribed medication delivery regimen and stored data corresponding to a history of doses when a dose has been missed and generate a corresponding reminder to the patient, and (c) transmit the history of doses to another external device.

8. The injection sensing device of claim 1, wherein the processing device is configured to associate time stamps with respective sensor data and to analyze the sensor data comprising sensed temperatures at the injection site and corresponding time stamps to determine flow rate of the medication from the medication delivery device to the patient.

9. The injection sensing device of claim 1, wherein the processing device is configured to generate a curve representing determined changes in sensed temperatures at the injection site over time and calculate area under the curve to estimate a delivered dose from the medication delivery device.

10. The injection sensing device of claim 1, wherein the processing device is configured to determine delivery infomatics using the sensor data comprising at least one of completion of medication delivery, completion of prescribed dosage, total amount of medication delivered, and time of medication delivery.

11. The injection sensing device of claim 1, wherein the medication delivery device is one of a syringe and a pen injector.

12. The injection sensing device of claim 1, further comprising a cutout section through the medicine delivery device can inject medicine into the skin of the patient, the cutout section being covered by a layer of material configured to retain consistent temperature of the patient's skin in the cutout section.

13. The injection sensing device of claim 1, further comprising a layer of material comprising arrangement of at least one of perforations or markings, the layer of material being disposed over an area of the patient's body comprising the injection site, the arrangement being configured to guide the patient where to inject.

14. The injection sensing device of claim 13, wherein the arrangement comprises a plurality of the perforations or markings spaced a designated amount from each other, the designated amount selected to reduce development of lipodystrophy in the area of the patient's body.

15. The injection sensing device of claim 2, wherein at least one of the processing device and the external device is configured to use the sensor data to determine estimated total amount of medication delivered.

16. The injection sensing device of claim 15, wherein at least one of the processing device and the external device is configured to compare the estimated total amount of medication delivered with a prescribed medication dosage, and to operate an indicator to indicate when the estimated total amount of medication delivered is less than the prescribed medication dosage.

* * * * *